United States Patent
Suzuki et al.

(10) Patent No.: US 6,303,801 B1
(45) Date of Patent: Oct. 16, 2001

(54) PROCESS FOR PRODUCING ALKYL-SUBSTITUTED HYDROQUINONES

(75) Inventors: Tomoyuki Suzuki, Tsukuba; Toshio Sasaki, Ichihara, both of (JP)

(73) Assignee: Sumitomo Chemical Company, Limited, Osaka (JP)

( * ) Notice: Subject to any disclaimer, the term of this patent is extended or adjusted under 35 U.S.C. 154(b) by 0 days.

(21) Appl. No.: 09/517,058

(22) Filed: Mar. 2, 2000

(30) Foreign Application Priority Data

Mar. 9, 1999 (JP) .................................................. 11-061539

(51) Int. Cl.⁷ ........................... C07C 50/04; C07C 50/38; C07C 37/00
(52) U.S. Cl. ........................... 552/293; 552/309; 568/804
(58) Field of Search ............................. 568/804; 552/293, 552/309

(56) References Cited

U.S. PATENT DOCUMENTS

| | | | |
|---|---|---|---|
| 4,060,561 | 11/1977 | Starks | 260/621 E |
| 5,847,237 | 12/1998 | Yago et al. | 568/804 |

FOREIGN PATENT DOCUMENTS

| | | | |
|---|---|---|---|
| 2670778A | 6/1992 | (FR) | 508/804 |
| 5872530 | 4/1983 | (JP) | 568/804 |
| 7265710 | 10/1995 | (JP) | 568/804 |

OTHER PUBLICATIONS

Notes—Kikumasa Sato et al; Synthesis of Trimethylhydroquinone; Jul., 1993; vol. 28; pp. 1928–1929.

Suzuki et al, Chemical Abstracts, vol. 131, No. 13, abstract No. 170169c, XP002901142, Sep. 27, 1999.

Chandler et al, Chemical Abstracts, vol. 127, No. 21, abstract No. 294905b, XP002901143, Nov. 24, 1997.

Patent Abstracts of Japan, vol. 11, No. 60 (C–405) (2507), Feb. 24, 1987 and JP 61–221135 (A).

Patent Abstracts of Japan, vol. 7, No. 161 (C–176) (1306), Jul. 15, 1983 and JP 58–72530 (A).

*Primary Examiner*—Alan L. Rotman
*Assistant Examiner*—Raymond Covington
(74) *Attorney, Agent, or Firm*—Birch, Stewart, Kolasch & Birch, LLP

(57) ABSTRACT

A process for producing an alkyl-substituted hydroquinone, wherein said process comprises reacting a hydroquinone compound represented by the general formula (1)

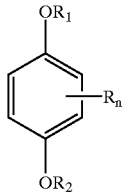

(1)

wherein $R_1$ and $R_2$ independently represent a hydrogen atom or a straight or branched chain alkyl group having 1 to 10 carbon atoms, R independently represent a straight or branched chain alkyl group having 1 to 10 carbon atoms and n represents an integer of 0 to 2, with a monohydric or dihydric alcohol in the presence of a catalyst and under the condition in which said alcohol is in a supercritical state by substitution of at least one hydrogen atom on the aromatic ring in said hydroquinone compound.

12 Claims, No Drawings

PROCESS FOR PRODUCING ALKYL-SUBSTITUTED HYDROQUINONES

BACKGROUND OF THE INVENTION

1. Field of the Invention

The present invention relates to a process for producing alkyl-substituted hydroquinone compounds.

2. Description of Related Art

Hydroquinone compounds having mono-, di- or trialkyl-substituted aromatic ring have been industrially used as raw materials or intermediates for pharmaceutical or agricultural chemicals, resins, various additives, polymerization inhibitors, industrial chemicals and the like. Particularly, trimethylhydroquinone has been widely used as an intermediate for vitamin E, a pharmaceutical, a polymerization inhibitor and a resin additive. In particular, it is much in demand as an intermediate for vitamin E.

Conventionally, it is known that hydroquinone compounds having alkyl-substituted aromatic ring are produced by gaseous phase reaction in which a hydroquinone compound and an alcohol are vaporized and passed through a catalyst phase or by liquid phase reaction utilizing the Friedel-Crafts reaction. For example, JP-A-7-265710 discloses a process for producing hydroquinone compound having methylated aromatic ring by reacting, in gaseous phase, hydroquinone and methanol using basic magnesium carbonate, a fine powder of phenol resin, manganese oxalate as a catalyst. This process, however, has a problem that it needs a complicated reaction apparatus. In addition, JP-A-58-72530 discloses a process for producing trimethylhydroquinone by contacting, in gaseous phase, hydroquinone and methanol heated to 400° C. with a catalyst such as iron oxide, manganese oxide, chromium oxide and the like. This process, however, has a problem that about 7% by mole of tetramethylhydroquinone is produced as a byproduct. Moreover, U.S. Pat. No. 4,060,561 discloses a process for producing trimethylhydroquinone from p-methoxyphenol and methanol.

In the known processes described above, the reaction is usually carried out in gaseous phase or in liquid phase. When the reaction is carried out in liquid phase, a strong catalyst such as a Lewis acid, phosphoric acid or the like is required causing a corrosion problem of apparatus. On the other hand, when the reaction is carried out in gaseous phase, there is a problem that the apparatus becomes complicated by the presence of preheating part, evaporation part, reaction part and condensing part and also needs to be large-sized.

It is desired for a process for producing a mixture of mono-, di- and trimethylhydroquinones from hydroquinone or mono- or dimethylhydroquinone and methanol with less production of tetramethylhydroquinone as a byproduct and allowing easier isolation and purification of trimethylhydroquinone which is a useful intermediate.

An object of the invention is to provide a process for producing hydroquinone compounds having alkyl-substituted aromatic ring from a hydroquinone compound and an alcohol without using a highly corrosive catalyst and allowing the reaction in a relatively small reactor.

An object of the invention is also to provide a process for producing a mixture of mono-, di- and trimethylhydroquinones from hydroquinone or mono- or dimethylhydroquinone and methanol with less production of tetramethylhydroquinone as a byproduct.

Under these circumstances, the present inventors have conducted an extensive study on a process for producing hydroquinone compounds having alkyl-substituted aromatic ring from hydroquinone compound sand alcohols. As the result, the present inventors have found that the above problems can be resolved by reacting hydroquinone compounds with alcohols which are in a supercritical state and thus completed the present invention.

SUMMARY OF THE INVENTION

That is, the present invention relates to a process (hereinafter, referred to as the process (I) of the invention) for producing an alkyl-substituted hydroquinone, wherein said process comprises reacting a hydroquinone compound represented by the general formula (1):

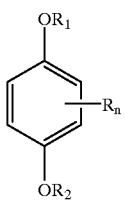

(1)

wherein $R_1$ and $R_2$ independently represent a hydrogen atom or a straight or branched chain alkyl group having 1 to 10 carbon atoms, R independently represent a straight or branched chain alkyl group having 1 to 10 carbon atoms and n represents an integer of 0 to 2, with a monohydric or dihydric alcohol in the presence of a catalyst and under the condition in which said alcohol is in a supercritical state by substitution of at least one hydrogen atom on the aromatic ring in said hydroquinone compound.

Further, the present invention relates to a process (hereinafter, referred to as the process (II) of the invention) for producing an alkyl-substituted hydroquinone, wherein said process comprises reacting the hydroquinone compound represented by the general formula (1) with a monohydric or dihydric alcohol in the presence of a catalyst and carbon dioxide and under the condition in which a mixture of said alcohol and carbon dioxide is in a supercritical state.

DETAILED DESCRIPTION OF THE INVENTION

The present invention is described below in detail.

In the hydroquinone compound represented by the general formula (1), used as the starting material of the present invention, $R_1$ and $R_2$ include a straight or branched chain alkyl group having 1 to 10 carbon atoms, such as a methyl group, an ethyl group, n-propyl group, isopropyl group, n-butyl group, isobutyl group, t-butyl group and the like, and a hydrogen atom. R in the hydroquinone compound is not present or one or two of R is present on the aromatic ring. R includes a straight or branched chain alkyl group having 1 to 10 carbon atoms, such as a methyl group, an ethyl group, n-propyl group, isopropyl group, n-butyl group, isobutyl group, t-butyl group and the like. Specific examples of the hydroquinone compound represented by the general formula (1) include hydroquinone, monomethylhydroquinone, monoethylhydroquinone, 2,3-dimethylhydroquinone, 2,5-dimethylhydroquinone, 2,6-dimethylhydroquinone, p-methoxyphenol, 1,4-dimethoxybenzene and the like. Among them, one compound or a plurality of compounds can be used.

The alcohol, the other starting material in the present invention, is not particularly limited as far as it is a monohydric or dihydric alcohol, and preferably, a monohydric alcohol represented by the general formula (2):

$$R_3\text{—OH} \qquad (2)$$

wherein $R_3$ represents a straight or branched chain alkyl group having 1 to 10 carbon atoms. $R_3$ includes a methyl group, an ethyl group, n-propyl group, isopropyl group, n-butyl group, isobutyl group, t-butyl group and the like.

Examples of the monohydric alcohol represented by the general formula (2) specifically include methanol, ethanol, n-propanol, isopropanol, n-butanol, isobutanol, t-butanol, pentanol, hexanol, heptanol, n-octanol, n-nonanol, n-decanol and the like. Among them, methanol, ethanol, n-propanol and n-butanol are preferred, methanol and ethanol are more preferred and methanol is further preferred.

Examples of the dihydric alcohol include ethylene glycol, propylene glycol and the like.

The hydroquinone compound and the alcohol, respectively, may be used independently or in combination thereof. The molar ratio of the alcohol to the hydroquinone compound is selected according to compounds used. Generally, it is 3 to 1,000 and preferably 3 to 300.

In the present invention, at least one hydrogen atom of aromatic ring is usually substituted by alkyl group derived from a monohydric or dihydric alcohol.

In the process (I) and the process (II) of the present invention, when hydroquinone as the hydroquinone compound and methanol as the alcohol are used, respectively, a mixture of monomethylhydroquinone, dimethylhydroquinone and trimethylhydroquinone is obtained as a mixture of hydroquinone compounds having mono-, di- and trialkyl-substituted aromatic ring. The ratio of said substituted compounds in the mixture depends on the reaction conditions such as temperature, pressure and so on. In addition, there may be a case wherein any one or two of said substituted compounds are not contained in said mixture and a case wherein any other byproducts are contained.

The process (I) of the present invention is characterized in that the reaction is carried out under the condition in which the alcohol is supercritical state. In addition, the process (II) of the present invention is characterized in that the reaction is carried out under the condition in which a mixture of the alcohol and carbon dioxide is supercritical state.

The supercritical state referred to in the invention means the following state:

In addition to the three states, gas, liquid and solid state, in which substances exist, there is a fluid state in which a substance does not condense by pressure when the condition is shifted over the critical temperature and the critical pressure. This state is referred to as the supercritical state.

A fluid in the supercritical state shows properties different from the normal properties of a liquid and gas. The density of a fluid in the supercritical state is approximate to that of a liquid and the viscosity of said fluid is approximate to that of a gas. The thermal conductivity and the diffusion coefficient are intermediate value of gas and liquid. It is "a solvent other than a liquid". It is favorable for migration of substances due to a low viscosity and a high diffusion. In addition, a high heat shifting can be attained due to a high conductivity.

When the supercritical state is used as the field of reaction, a higher reactivity than that in the normal gaseous phase reaction can be obtained because the field of reaction is in the high density and high diffusion state as described above, and thus it is possible to produce hydroquinone compounds having alkyl-substituted aromatic ring at a relatively low temperature.

Since the supercritical fluid itself provides a high reactivity, a desired compound can be produced without a highly corrosive catalyst and at a temperature at which reaction substrates are not decomposed.

In addition, since the supercritical state has a density approximate to that of a liquid phase, the reaction apparatus can be smaller than that in the gaseous phase reaction.

In the present invention, the upper limit of the reaction temperature is not limited and preferably 450° C. or less in order to avoid decomposition of the hydroquinone compound. The upper limit of the reaction pressure is again not limited and preferably 25 MPa or less because increase in the pressure resistance of the reaction apparatus is costly.

The process (I) of the present invention requires that the reaction is carried out under the condition in which the alcohol is in the supercritical state. When methanol is used as the alcohol, the reaction is carried out at 240° C. or more and 8 MPa or more, because methanol has the critical temperature of 240° C. and the critical pressure of 8 MPa. When ethanol is used as the alcohol, the reaction is carried out at 243° C. or more and 6.3 MPa or more, because ethanol has the critical temperature of 243° C. and the critical pressure of 6.3 MPa. When n-propanol is used as the alcohol, the reaction is carried out at 264° C. or more and 5 MPa or more, because n-propanol has the critical temperature of 264° C. and the critical pressure of 5 MPa. When n-butanol is used as the alcohol, the reaction is carried out at 287° C. or more and 4.8 MPa or more, because n-butanol has the critical temperature of 287° C. and the critical pressure of 4.8 MPa.

The process (II) of the invention is described below.

The process (II) of the invention requires that the reaction is carried out in the presence of carbon dioxide and under the condition in which a mixture of the mono- or dihydric alcohol and carbon dioxide is in the supercritical state.

The mixing ratio of said alcohol and carbon dioxide is not particularly limited and decided according to the solubility of the hydroquinone compound used in the reaction in said alcohol. A preferred mixing ratio of said alcohol and carbon dioxide is 10:90 to 90:10.

Specific description will be given for a case wherein methanol as the alcohol and hydroquinone as the hydroquinone compound are used. For example, when the molar ratio of methanol and carbon dioxide is 75:25, the critical temperature and the critical pressure of said mixture is 204° C. and 12.75 MPa, respectively, according to a literature (J. Chem. Thermodynamics, vol. 23, page 970 (1991)).

When the production of hydroquinone compound having methyl-substituted aromatic ring is conducted under a temperature-pressure conditions in which a mixture of methanol and carbon dioxide is in a supercritical state, it is necessary to place said mixture under a temperature-pressure conditions in which said mixture is in a supercritical state. For example, when the molar ratio of methanol and carbon dioxide is 75:25, it is necessary to conduct the reaction at a temperature of 204° C. or more and at a pressure of 12.75 MPa or more, preferably at a temperature of 240° C. or more and at a pressure of 12.75 MPa or more.

The reaction period for the process (I) the process (II) of the present invention is suitably selected according to the kind of the hydroquinone compound and the alcohol, respectively, and is usually within a range of 5 minutes to 24 hours.

In addition, the respective reactions are required to be conducted in the presence of a catalyst. Usable catalyst is not particularly limited insofar as it is capable of promoting the alkylation in the aromatic ring and includes, for example, acids, alkalis, metal powders, metal oxides and the like.

Representative examples of acids include acetic acid, formic acid, propionic acid, benzoic acid and the like which are not limitative.

In addition, they can be used in combination with a metal powder or a metal oxide.

Suitably used alkalis include alkali metal hydroxides and alkali metal alkoxides. Preferred example of said alkali metal hydroxides are lithium hydroxide, sodium hydroxide and potassium hydroxide.

Preferred example of said alkali metal alkoxides are lithium methylate, sodium methylate and potassium methylate.

In addition, they can be used in combination with a metal powder or a metal oxide.

Representative examples of metal oxides include oxides of Mg, Ca, V, Cr, Mn, Fe, Ni, Cu, Zn, Ge, Al, Pt, Pb, Ru, W, La, Sm, Hf and the like, which are not limitative.

Specific examples include MgO, CaO, $V_2O_5$, $Cr_2O_3$, $MnO_2$, $Fe_2O_3$, FeO, $Fe_3O_4$, NiO, CuO, $Cu_2O$, ZnO, $GeO_2$, GeO, $Al_2O_3$, PtO, $PtO_2$, $Pb_3O_4$, $RuO_2$, $WO_2$, $WO_3$, $La_2O_3$, $Sm_2O_3$, $HfO_2$ and the like. Preferred examples are CaO (calcium oxide), $MnO_2$ (manganese dioxide), $Cr_2O_3$ (chromium oxide), ZnO (zinc oxide), MgO (magnesium oxide), $La_2O_3$ (lanthanum oxide), $GeO_2$ (germanium oxide) and $Fe_2O_3$ (iron oxide).

In addition, a plurality of metal oxides can be combined and the oxide can be used in combination with a metal powder, an acid or an alkali.

Representative examples of metal powders include powder of Mg, Ca, Cr, Mn, Fe, Ni, Cu, Zn, Ge, Al, Pt, Pb and the like, among which Zn powder (zinc powder) is preferred.

In addition, a plurality of metal powders can be combined and the powder can be used in combination with a metal oxide, an acid or an alkali.

The present invention can be carried out in various modes of embodiment for reaction. For example, the invention may be carried out in batch system or in continuous system.

Hydroquinone compounds having mono-, di- or trialkyl-substituted aromatic ring are separated to various purities required for desired use from a reaction mixture after the reaction according to the process (I) or the process (II) of the present invention, respectively. Said reaction mixture sometimes contains unreacted raw materials or other impurities in addition to hydroquinone compounds having mono-, di- or trialkyl-substituted aromatic ring.

The method for the separation is not particularly limited and general procedures such as distillation, extraction and the like are applied depending on properties of respective substituted compounds.

Specifically, when hydroquinone and methanol are used, a mixture of monomethylhydroquinone, dimethylhydroquinone and trimethylhydroquinones is obtained. By subjecting the mixture to separation procedure by means of rectification, extraction, adsorption and the like, monomethylhydroquinone, dimethylhydroquinone and trimethylhydroquinone, respectively, can be obtained in separated form.

Therefore, the present invention allows to provide a process for producing hydroquinone compounds having alkyl-substituted aromatic ring from a hydroquinone compound and an alcohol without using a highly corrosive catalyst and allowing the reaction in a relatively small reactor and at a relatively low temperature. In addition, when hydroquinone and methanol are used as raw materials, trimethylhydroquinone, which is useful as an intermediate materialforvitamin E, can be obtained bysubjecting a mixture of mono-, di- and trimethylhydroquinones containing less tetramethylhydroquinone obtained after the completion of the reaction to separation and purification procedures from hydroquinone or mono- or dimethylhydroquinone and methanol.

According to the present invention, it is possible to provide a process for producing hydroquinone compounds having alkyl-substituted aromatic ring from a hydroquinone compound and an alcohol without using a highly corrosive catalyst and allowing the reaction in a relatively small reactor and at a relatively low temperature.

In addition, when hydroquinone and methanol are used as raw materials, it is possible to produce a mixture of mono-, di- and trimethylhydroquinones containing less tetramethylhydroquinone from hydroquinone or mono- or dimethylhydroquinone and methanol, and the product can be used as raw materials or intermediates for pharmaceutical or agricultural chemicals, resins, various additives, polymerization inhibitors, industrial chemicals and the like by subjecting to separation and purification procedures.

EXAMPLES

The present invention will now be described in more detail by examples, which should not be construed as a limitation upon the scope of the invention.

The amounts of the reactants and the products are obtained by the area percentage method based on the signal intensities of respective substances detected with the gas chromatography apparatus GC-353B (manufactured by GL Science Co.).

Example 1

Into an autoclave (inner volume: 9 ml, made of Stainless Steel (SUS 316), equipped with amanometer) were charged 0.112 g of methylhydroquinone (manufactured by Wako Pure Chemical Ind., Ltd.), 3.372 g of methanol (extra fine reagent grade, manufactured by Wako Pure Chemical Ind., Ltd.) and 0.2 mg of sodium methylate (manufactured by Wako Pure Chemical Ind., Ltd.). The reaction was started by elevating the temperature up to 350° C. with sand bath. The pressure during the reaction was 16 MPa. After 2 hours, the autoclave was quickly cooled and the reaction solution was taken out from the autoclave when the temperature was cooled back to the room temperature. The measurement according to the process described above revealed that the conversion of methylhydroquinone was 59% by mole, the selectivity of dimethylhydroquinone was 69% by mole, the selectivity of trimethylhydroquinone was 10% by mole and no tetramethylhydroquinone was produced.

As byproducts, methyl ethers of monomethylhydroquinone, represented by the formulae shown below, were formed with a total selectivity of 4%.

methyl ethers of monomethylhydroquinone

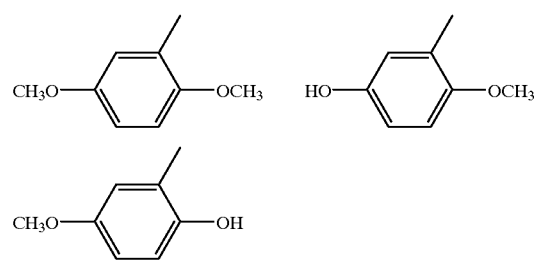

methyl ethers of dimethylhydroquinone

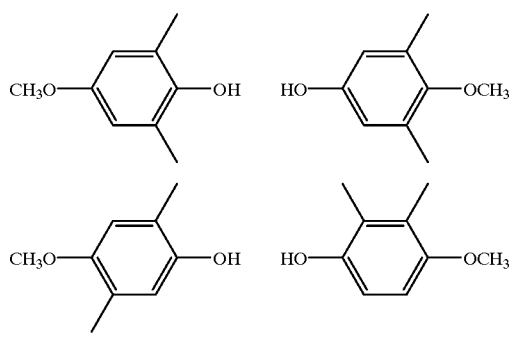

methyl ethers of trimethylhydroquinone

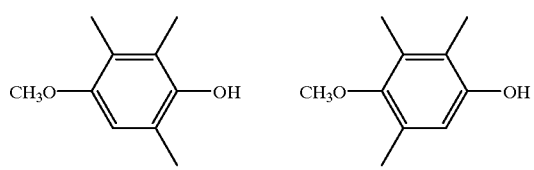

Example 2

Into an autoclave (inner volume: 9 ml, made of SUS 316, equipped with a manometer) were charged 0.108 g of methylhydroquinone, 3.573 g of methanol and 0.2 mg of sodium methylate. The reaction was started by elevating the temperature up to 350° C. with sand bath. The pressure during the reaction was 16 MPa. After 4 hours, the autoclave was quickly cooled and the reaction solution was taken out from the autoclave when the temperature was cooled back to the room temperature. The measurement according to the process described above revealed that the conversion of methylhydroquinone was 86% by mole, the selectivity of dimethylhydroquinone was 38% by mole, the selectivity of trimethylhydroquinone was 37% by mole and no tetramethylhydroquinone was produced. As byproducts, methyl ethers of monomethylhydroquinone, dimethylhydroquinone and trimethylhydroquinone, represented by the formulae shown above, were formed with a selectivity of 6%, 4% and 3%, respectively.

Example 3

Into an autoclave (inner volume: 9 ml, made of SUS 316, equipped with a manometer) were charged 0.111 g of methylhydroquinone, 3.463 g of methanol and 4.6 mg of manganese dioxide (manufactured by High Purity Chemicals Co.). The reaction was started by elevating the temperature up to 350° C. with sand bath. The pressure during the reaction was 16 MPa. After 2 hours, the autoclave was quickly cooled and the reaction solution was taken out from the autoclave when the temperature was cooled back to the room temperature. The measurement according to the process described above revealed that the conversion of methylhydroquinone was 45% by mole, the selectivity of dimethylhydroquinone was 64% by mole, the selectivity of trimethylhydroquinone was 17% by mole and no tetramethylhydroquinone was produced. As byproducts, methyl ethers of dimethylquinone and trimethylquinone, represented by the formulae shown above, were formed with a selectivity of 6% and 2%, respectively.

Example 4

Into an autoclave (inner volume: 9 ml, made of SUS 316, equipped with a manometer) were charged 0.105 g of hydroquinone (manufactured by Wako Pure Chemical Ind., Ltd.), 3.602 g of methanol and 1.3 mg of manganese dioxide (manufactured by High Purity Chemicals Co.). The reaction was started by elevating the temperature up to 350° C. with sand bath. The pressure during the reaction was 15 MPa. After 8 hours, the autoclave was quickly cooled and the reaction solution was taken out from the autoclave when the temperature was cooled back to the room temperature. The measurement according to the process described above revealed that the conversion of hydroquinone was 41% by mole, the selectivity of monomethylhydroquinone was 43% by mole, the selectivity of dimethylhydroquinone was 13% by mole and the selectivity of trimethylhydroquinone was 1% by mole. No tetramethylhydroquinone was produced.

Example 5

Into an autoclave (inner volume: 9 ml, made of SUS 316, equipped with a manometer) were charged 0.104 g of methylhydroquinone, 3.4078 g of methanol and 8.3 mg of iron powders (manufactured by Wako Pure Chemical Ind., Ltd.). The reaction was started by elevating the temperature up to 350° C. with sand bath. The pressure during the reaction was 20 MPa. After 2 hours, the autoclave was quickly cooled and the reaction solution was taken out from the autoclave when the temperature was cooled back to the room temperature. The measurement according to the process described above revealed that the conversion of methylhydroquinone was 16% by mole, the selectivity of dimethylhydroquinone was 82% by mole and the selectivity of trimethylhydroquinone was 3% by mole. No tetramethylhydroquinone was produced.

Example 6

Into an autoclave (inner volume: 9 ml, made of SUS 316, equipped with a manometer) were charged 0.115 g of methylhydroquinone, 3.268 g of methanol and 4.6 mg of chromium oxide (manufactured by High Purity Chemicals). The reaction was started by elevating the temperature up to 350° C. with sand bath. The pressure during the reaction was 18 MPa. After 2 hours, the autoclave was quickly cooled and the reaction solution was taken out from the autoclave when the temperature was cooled back to the room temperature. The measurement according to the process described above revealed that the conversion of methylhydroquinone was 17% by mole, the selectivity of dimethylhydroquinone was 74% by mole and the selectivity of trimethylhydroquinone was 2% by mole. No tetramethylhydroquinone was produced.

Example 7

Into an autoclave (inner volume: 9 ml, made of SUS 316, equipped with a manometer) were charged 0.092 g of methylhydroquinone, 3.895 g of methanol and 7.2 mg of zinc powders (manufactured by High Purity Chemicals Co.). The reaction was started by elevating the temperature up to 350° C. with sand bath. The pressure during the reaction was 17 MPa. After 2 hours, the autoclave was quickly cooled and the reaction solution was taken out from the autoclave when the temperature was cooled back to the room temperature. The measurement according to the process described above revealed that the conversion of methylhydroquinone was 23% by mole, the selectivity of dimethylhydroquinone was 92% by mole, the selectivity of trimethylhydroquinone was 8% by mole and no tetramethylhydroquinone was produced.

Example 8

Into an autoclave (inner volume: 9 ml, made of SUS 316, equipped with a manometer) were charged 0.098 g of methylhydroquinone, 3.491 g of methanol and 7 mg of lanthanum oxide (manufactured by High Purity Chemicals Co.). The reaction was started by elevating the temperature up to 350° C. with sand bath. The pressure during the reaction was 18 MPa. After 2 hours, the autoclave was quickly cooled and the reaction solution was taken out from the autoclave when the temperature was cooled back to the room temperature. The measurement according to the process described above revealed that the conversion of methylhydroquinone was 32% by mole, the selectivity of dimethylhydroquinone was 80% by mole, the selectivity of trimethylhydroquinone was 10% by mole and no tetramethylhydroquinone was produced.

Example 9

Into an autoclave (inner volume: 4.5 ml, made of SUS 316, without manometer) were charged 0.031 g of hydroquinone, 1.370 g of methanol and 0.063 mg of lithium hydroxide monohydrate (manufactured by Wako Pure Chemical Ind., Ltd.). The reaction was started by elevating the temperature up to 420° C. with sand bath. After 7 minutes, the autoclave was quickly cooled and the reaction solution was taken out from the autoclave when the temperature was cooled back to the room temperature. The measurement according to the process described above revealed that the conversion of hydroquinone was 72% by mole, the selectivity of monomethylhydroquinone was 34% by mole, the selectivity of dimethylhydroquinone was 42% by mole and the selectivity of trimethylhydroquinone was 18% by mole. As byproducts, tetramethylhydroquinone and p-methoxyphenol were produced with selectivities of 2% by mole and 1% by mole, respectively.

Because the autoclave used here has no manometer, the following experiment was carried out in order to estimate the pressure during the reaction:

The same autoclave was connected to manometer, charged with the same amounts of hydroquinone and methanol, heated to 420° C. and the pressure was measured.

The estimated value of the pressure during the reaction was 18 MPa.

Example 10

Into an autoclave (inner volume: 4.5 ml, made of SUS 316, without manometer) were charged 0.030 g of hydroquinone, 1.350 g of methanol and 0.100 mg of lithium hydroxide monohydrate. The reaction was started by elevating the temperature up to 350° C. with sand bath. After 2 hours, the autoclave was quickly cooled and the reaction solution was taken out from the autoclave when the temperature was cooled back to the room temperature. The measurement according to the process described above revealed that the conversion of hydroquinone was 84% by mole, the selectivity to monomethylhydroquinone was 37% by mole, the selectivity of dimethylhydroquinone was 41% by mole and the selectivity of trimethylhydroquinone was 16% by mole. As byproducts, tetramethylhydroquinone, p-methoxyphenol and the ethers of monomethylhydroquinone represented by the formulae shown above were produced with selectivities of 2% by mole, 1% by mole and 1% by mole, respectively.

Because the autoclave used here has no manometer, the following experiment was carried out in order to estimate the pressure during the reaction:

The same autoclave was connected to manometer, charged with the same amounts of hydroquinone and methanol, heated to 350° C. and the pressure was measured.

The estimated value of the pressure during the reaction was 10.5 MPa.

Example 11

Into an autoclave (inner volume: 4.5 ml, made of SUS 316, without manometer) were charged 0.016 g of hydroquinone, 1.355 g of methanol and 2.5 mg of calcium oxide (manufactured by Wako Pure Chemical Ind., Ltd.). The reaction was started by elevating the temperature up to 425° C. with sand bath. After 8 minutes, the autoclave was quickly cooled and the reaction solution was taken out from the autoclave when the temperature was cooled back to the room temperature. The measurement according to the process described above revealed that the conversion of hydroquinone was 87% by mole, the selectivity of monomethylhydroquinone was 30% by mole, the selectivity of dimethylhydroquinone was 42% by mole and the selectivity of trimethylhydroquinone was 18% by mole. As byproducts, tetramethylhydroquinone was produced with a selectivity of 3% by mole.

Because the autoclave used here has no manometer, the following experiment was carried out in order to estimate the pressure during the reaction:

The same autoclave was connected to manometer, charged with the same amounts of hydroquinone and methanol, heated to 425° C. and the pressure was measured.

The estimated value of the pressure during the reaction was 18.2 MPa.

What is claimed is:

1. A process for producing an alkyl-substituted hydroquinone, wherein said process comprises reacting a hydroquinone compound represented by the general formula (1):

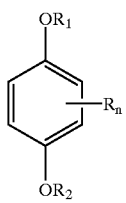

(1)

wherein $R_1$ and $R_2$ independently represent a hydrogen atom or a straight or branched chain alkyl group having 1 to 10 carbon atoms, R independently represent a straight or branched chain alkyl group having 1 to 10 carbon atoms and n represents an integer of 0 to 2, with a monohydric or dihydric alcohol in the presence of a catalyst and under the condition in which said alcohol is in a supercritical state, by substitution of at least one hydrogen atom on the aromatic ring in said hydroquinone compound of the general formula (1).

2. The process according to claim 1, wherein the hydroquinone compound represented by the general formula (1) is reacted with a monohydric or dihydric alcohol in the presence of a catalyst and carbon dioxide and under the condition in which a mixture of said alcohol and carbon dioxide is in a supercritical state.

3. The process according to claim 1, wherein the hydroquinone compound represented by the general formula (1) is at least one selected from the group consisting of hydroquinone, monomethylhydroquinone and dimethylhydroquinone.

4. The process according to claim 1, wherein the monohydric alcohol is an alcohol represented by the general formula (2):

$$R_3\text{—OH} \qquad (2)$$

wherein $R_3$ represents a straight or branched chain alkyl group having 1 to 10 carbon atoms.

5. The process according to claim 4, wherein $R_3$ in the general formula (2) is a methyl group or an ethyl group.

6. The process according to claim 4, wherein $R_3$ in the general formula (2) is a methyl group.

7. The process according to claim 1, wherein the catalyst is an acid, an alkali, a metal powder or a metal oxide.

8. The process according to claim 7, wherein the alkali is an alkali metal hydroxide or an alkali metal alkoxide.

9. The process according to claim 8, wherein the alkali metal hydroxide is lithium hydroxide, sodium hydroxide or potassium hydroxide.

10. The process according to claim 8, wherein the alkali metal alkoxide is lithium methylate, sodium methylate or potassium methylate.

11. The process according to claim 7, wherein the metal oxide is calcium oxide, manganese dioxide, chromium oxide, zinc oxide, magnesium oxide, lanthanum oxide, germanium oxide or iron oxide.

12. The process according to claim 7, wherein the metal powder is zinc powder.

* * * * *